US007659982B2

(12) United States Patent
Baillet et al.

(10) Patent No.: US 7,659,982 B2
(45) Date of Patent: Feb. 9, 2010

(54) QUANTITATIVE EVALUATION OF A COLOR FILTER

(75) Inventors: Gilles Baillet, Charenton le Pont (FR); Bernard Bourdoncle, Charenton le Pont (FR); Margalith Harrar, Charenton le Pont (FR); Françoise Vienot, Paris (FR)

(73) Assignee: Essilor International (Compagnie Generale d'Optique), Charenton le Pont (FR)

( * ) Notice: Subject to any disclaimer, the term of this patent is extended or adjusted under 35 U.S.C. 154(b) by 377 days.

(21) Appl. No.: 11/839,099

(22) Filed: Aug. 15, 2007

(65) Prior Publication Data

US 2008/0046207 A1 Feb. 21, 2008

(30) Foreign Application Priority Data

Aug. 16, 2006 (FR) .................................. 06 07323

(51) Int. Cl.
*G01N 21/25* (2006.01)
(52) U.S. Cl. ....................................... 356/406
(58) Field of Classification Search ........................ None
See application file for complete search history.

(56) References Cited

U.S. PATENT DOCUMENTS

| 5,418,419 | A | 5/1995 | McGuire |
| 6,373,573 | B1 * | 4/2002 | Jung et al. ................... 356/419 |
| 6,959,157 | B2 * | 10/2005 | Nakayama ................... 399/39 |
| 2003/0053063 | A1 | 3/2003 | Vienot et al. |

FOREIGN PATENT DOCUMENTS

| EP | 1 273 894 | 1/2003 |
| JP | 2001297323 | 10/2001 |

OTHER PUBLICATIONS

Harrar et al., "Comparison of Color Appearance Changes Assessed by Observers Versus Predicted by CIECAM02," *AIC Colour 05-10th Congress of the International Colour Association*, pp. 643-646.
Alessi et al., "A Colour Appearance Model for Colour Management Systems: CIECAM02," *CIE Technical Report*, ISBN 3 901 906 29 0 (2004).

* cited by examiner

*Primary Examiner*—Tu T Nguyen
(74) *Attorney, Agent, or Firm*—Occhiuti Rohlicek & Tsao LLP

(57) ABSTRACT

A quantitative evaluation of a color filter (10) in accordance with the capacity of said filter to restore hues comprises the use of a numerical color appearance model. Values of a perceptive attribute are calculated for hue samples (20), by simulating the observation of each of the samples through the filter (10) and without a filter. The values of the perceptive attribute correspond to the visual perception of the samples by an observer (40), and a deviation between the values with and without filter constitutes the result of the evaluation of the filter. Such a method makes it possible to quantitatively rank several color filters, and the ranking obtained corresponds to that which would be established by real observers evaluating the filters.

11 Claims, 3 Drawing Sheets

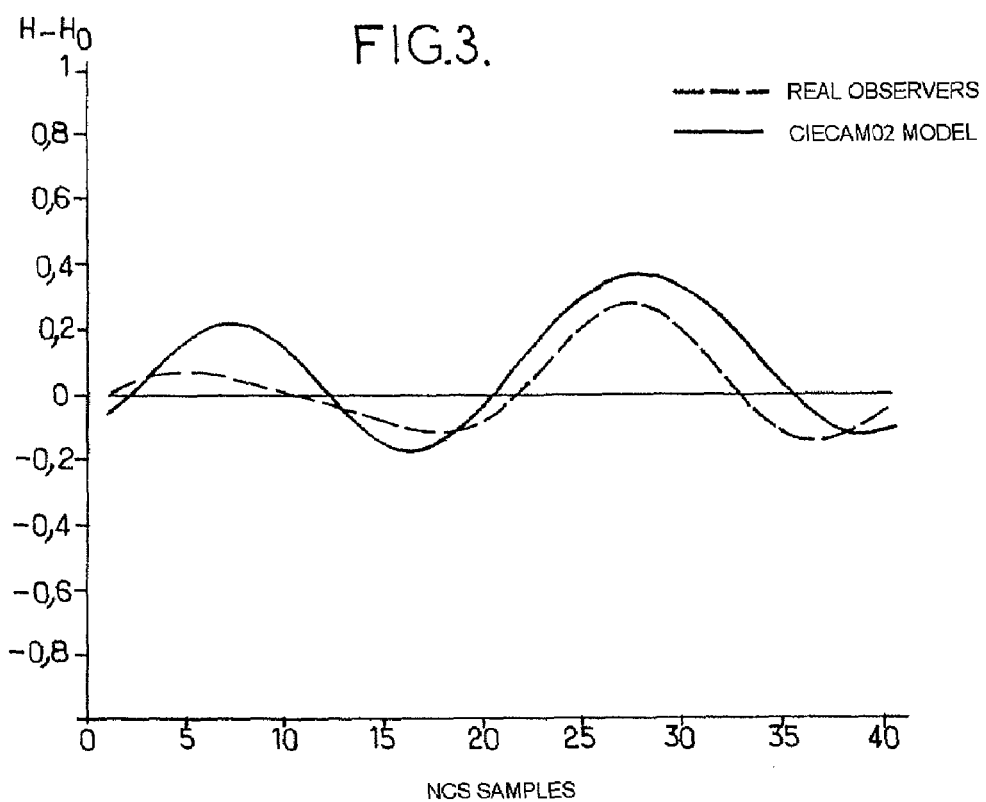
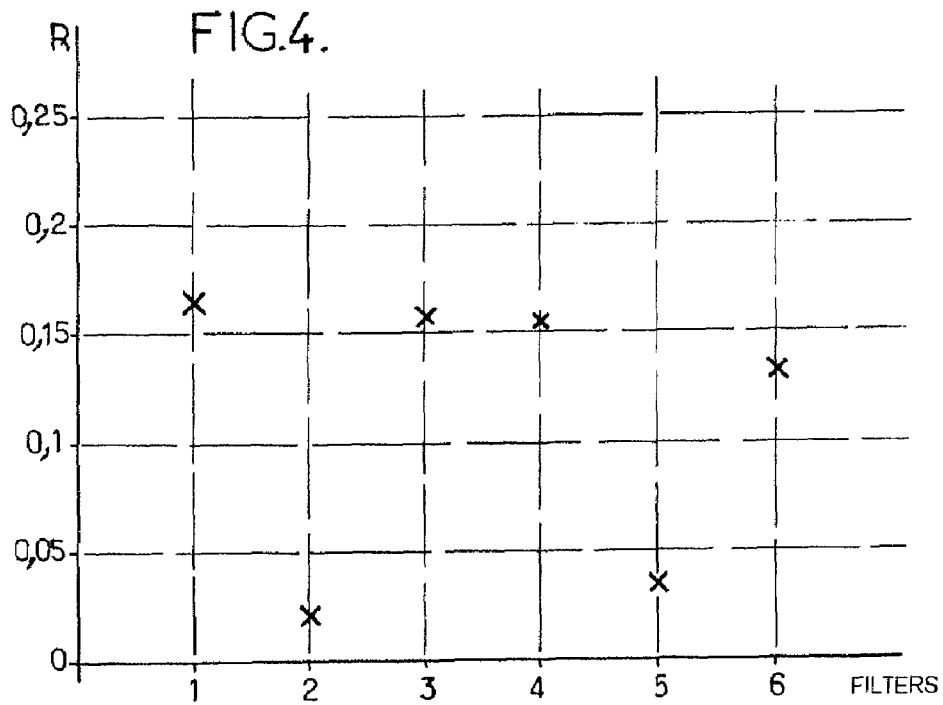

QUANTITATIVE EVALUATION OF A COLOR FILTER

CROSS-REFERENCE TO RELATED APPLICATIONS

This application claims the benefit of French Application No. 06 07323, filed Aug. 16, 2006, the content of which is hereby incorporated by reference in its entirety.

The present invention relates to a method of quantitatively evaluating a color filter. It may be applied, in particular, to evaluate a restitution of hues by a tinted ophthalmic lens.

Color filters are used in numerous applications, for example to attenuate an overly large luminous intensity or to increase an image contrast. In particular, tinted ophthalmic lenses, especially solar protection lenses, are color filters which are intended to be fitted into a spectacle frame.

Theoretically, a filter can exhibit a transmission spectrum which is substantially flat in the visible light interval 380 nm-780 nm (nanometer). It ought then not to modify the perception of hues of reference samples, between an observation of these samples through the filter and a direct observation of the same samples, that is to say without the filter. However, such a filter with flat spectrum is not achievable in practice, especially on account of spectral limitations of the dyes which are used to manufacture filters. Moreover, its grey appearance would be rather unaesthetic and rather unappealing for ophthalmic applications.

The transmission spectra in the visible light interval of the filters which are used in practice therefore exhibit variations. They are then liable to modify the perception of hues by an observer, between a direct observation of samples of these hues and an observation of them through the filter. For this reason, they are called color filters.

It is then necessary to quantitatively evaluate the restitution of hues by a color filter, especially in order to discriminate filters which would modify the perception of hues in an overly significant or even detrimental manner. Such a requirement exists most particularly in respect of ophthalmic lenses providing protection from the sun, which are used outdoors, that is to say under conditions where a natural rendition is desired for a large number of hues present in our environment.

Document EP 1,273,894 proposes a method of evaluating colors of filters, which is based on calculating chromatic deviations expressed in the CIELAB space, labelled by the axes L*, a*, b*, and defined by the Commission Internationale de l'Eclairage. The involvement of observers is then no longer necessary, for visually evaluating samples of hues viewed through the filters. However, the mode of evaluating the modification of the hues by each filter which is described in this document gives a poor account of the impression, for a human observer, of a rendition of hues which is natural.

An object of the present invention therefore consists in proposing a quantitative evaluation of a color filter, which does not have the drawbacks cited above.

To this end, the invention proposes a method which comprises the following steps:

/1/ measuring a transmission spectrum of a color filter over a visible light interval using a spectrophotometer;

/2/ obtaining, on the basis of the transmission spectrum of the filter and of a reflection spectrum of a reference hue sample, optical data which relate to a simulation of an observation of the hue sample through the filter;

/3/ introducing, into a numerical color appearance model, the optical data relating to the simulation of the observation of the hue sample through the filter, so as to obtain, for this sample, a value of at least one visual perceptive attribute; and /4/ calculating a deviation between the perceptive attribute value which is obtained for the simulation of the observation of the hue sample through the filter and a value of the same perceptive attribute for the same sample when the latter is observed without the filter, The deviation which is calculated in step /4/, between the perceptive attribute value which is obtained for the hue sample by simulating an observation of the latter through the filter and the value for an observation without the filter, constitutes an evaluation of the restitution of the hue of the reference sample by the color filter. Stated otherwise, this result of the evaluation characterizes the capacity of the filter to restore the hue in a natural manner, that is to say the impression of an observer to perceive the real hue through the filter.

Such a method of evaluating a color filter is economical and fast to implement, in particular because it does not necessitate any recourse to real observers. It merely requires spectrophotometric measurement means and calculation means which are simple and commonly available.

An important characteristic of the invention is the use, in step /3/, of a numerical model of appearance of hues. Such a model makes it possible to take account of physiological and subjective phenomena which are involved in the visual perception of hues by a human being. Variations in sensitivity of the human eye as a function of the hue itself or of other environmental parameters are thus taken into account, along with differences in assessment of hues which may result from psychological factors. The quantitative evaluation which is obtained according to the invention, to characterize the restitution of the hue of the sample by the color filter, consequently corresponds to a real evaluation, such as would be performed by a human observer.

According to a preferred mode of implementation of the invention, the numerical color appearance model, which is used in step /3/, may be the CIECAM02 model ("Color Appearance Model for Color Management Systems") defined in 2002 by the Commission Internationale de l'Eclairage in publications ISBN 3 901 906 290 and CIE 159: 2004. The inventors have then verified that the evaluations of color filters which are performed using a method according to the invention correspond in satisfactory measure to evaluations performed by a set of human observers.

According to a refinement of the invention, steps /2/ to /4/ may be repeated for several reference hue samples so as to obtain respective deviations of perceptive attribute for these hue samples. The method then comprises the following additional step:

/5/ calculating a value characterizing the global restitution of hues by the color filter on the basis of the set of perceptive attribute deviations which are obtained respectively for the hue samples used.

The evaluation which is then obtained of the restitution of hues by the color filter is based on several hues. It therefore makes it possible to evaluate the filter in a global manner while taking account of conditions of use which are varied, that is to say for a multiplicity of hues which are perceived through the filter.

In particular, the samples of reference hues may be selected from those which are referenced in the NCS system ("Natural Color System" see NCS Atlas 1950 Original). In particular, the inventors have shown that evaluations of any color filter which are performed on the basis of different series of NCS hue samples culminate in equivalent quantitative results, whereas these series are differentiated by values of clarity and saturation of the hues. Stated otherwise, a filter evaluation which is carried out according to the invention accounts correctly for the fact that the modification of a hue by a color filter depends little on the brightness and saturation of this hue.

The invention also proposes the use of an evaluating method as described previously to quantitatively evaluate the restitution of hues by a tinted ophthalmic lens. In this case, the refinement of the method which consists in using several samples of hues to evaluate the global restitution of hues by the ophthalmic lens is particularly advantageous. Indeed, the ophthalmic lens may be used by a wearer of the latter under highly varied conditions, which depend on his luminous environment and also the objects that he observes.

The invention further proposes a method of ranking color filters, whereby several color filters are evaluated successively using an evaluating method as described above. The filters may then be ranked as a function of the evaluation results which are obtained respectively for each of them. Such a ranking method is particularly useful when several filters have been manufactured, which exhibit different renditions of hues, and when one of them must be selected as a model for mass production. The ranking method according to the invention makes it possible to avoid the need for real observers to perform comparative tests of each of the filters. A significant time saving is thus obtained when designing the product.

In particular, such a ranking method may be used to rank tinted ophthalmic lenses, such as solar protection lenses. Specifically, the selection of a tinted lens as a function of its capacity to restore hues is a particularly important step in respect of the ophthalmic application.

Other features and advantages of the present invention will appear in the description hereinbelow of a nonlimiting exemplary implementation, with reference to the appended drawings, in which:

FIG. 3 is a comparison of two diagrams of perceptive attribute deviation values obtained for a color filter and for a series of samples of reference hues, respectively using an evaluating method according to the invention and using a set of human observers; and FIG. 4 illustrates the results of evaluating several color filters obtained using a method according to the invention.

Figure 1:
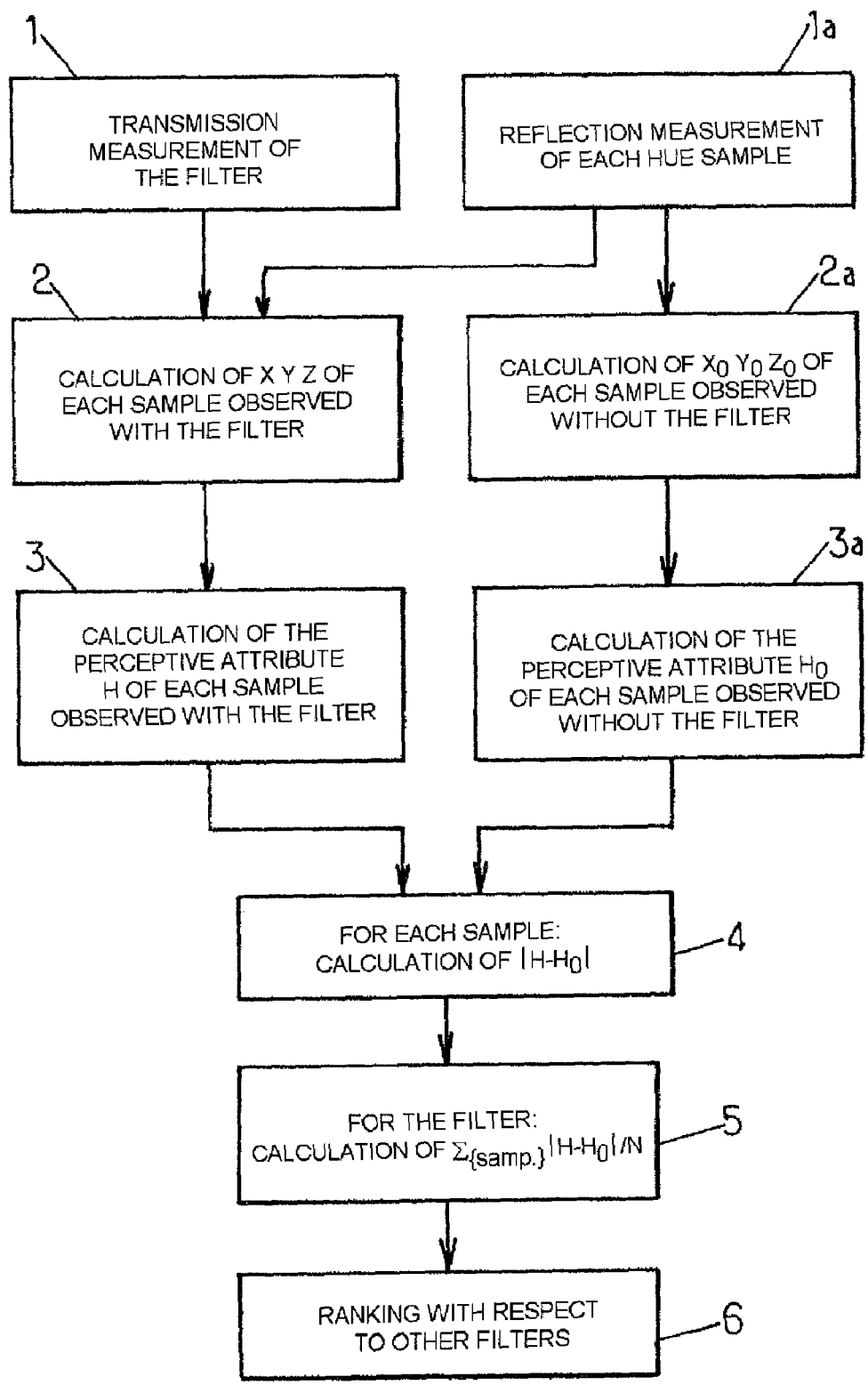
FIG. 1 is a schematic diagram of the steps of a method according to the invention, for evaluating a color filter.

An evaluation of a color filter in accordance with the invention is now described, with reference to FIG. 1.

During a first step referenced 1 in FIG. 1, a color filter is characterized in transmission using a spectrophotometer, which may be of a standard commercially available type. A transmission spectrum of the filter is thus obtained, which groups together transmission values measured for wavelengths distributed within a visible light interval. For example, the transmission of the filter may be measured over the wavelength interval 400 nm-700 nm with a spacing of 1 nm.

Samples of hues are moreover characterized spectrally in reflection. Such samples consist of opaque supports uniformly colored on one face. Preferably, standardized hue samples may be used, such as those which are fixed by the NCS system. These latter are distributed in series of 40 samples, each series corresponding to a variation of the hue of the samples, and the series being differentiated from one another by values of saturation ("chromativeness") and brightness (or else "1-blackness"). The samples of hues of one and the same series may be used to evaluate the color filter. A reflection spectrum of each of these samples is then obtained over the visible light wavelength interval 400 nm-700 nm (step 1a of FIG. 1). Preferably, the reflection spectrum of each hue sample is a nonspecular reflection spectrum, which corresponds better to real observation conditions, with respect to a specular reflection spectrum. Stated otherwise, the reflection spectra of the samples of hues correspond to values of angles of incidence and reflection of light which are different from those defined by the Bragg reflection conditions.

For each hue sample used, the spectral reflection values of the sample are combined with those for transmission of the filter and with spectral characteristics of an illuminating light source (step 2 of FIG. 1). Optical data are thus obtained, which characterize the hue sample when it is illuminated by the light source and observed simultaneously through the filter. In particular, the spectral characteristics which are used for the light source, also called the illuminant, may correspond to the "SoLux® Daylight" illumination conditions, a light source as described in patent U.S. Pat. No. 5,418,419. In the mode of implementation of the invention which is described here, the optical data which are obtained are the trichromatic components X, Y, Z relating to the simulation of the observation of the hue sample through the filter. The X, Y, Z components are calculated in a manner which is known to a person skilled in the art, using simple calculation means such as a personal computer. It is understood that in alternative modes of implementation of the invention, other optical data may be used in an equivalent manner. These optical data may be obtained by calculation or by any alternative experimental procedure, such as the use of a calorimetric photometer to directly measure the components X, Y, Z for example.

During step 3, the X, Y, Z components which correspond to the simulation of the observation of each hue sample through the filter are introduced into a numerical color appearance model. The inventors have validated experimentally that the CIECAM02 numerical model corresponds in a satisfactory manner to an average human visual perception. For this reason, the use of this model is preferred by the inventors. This numerical model, which may be implemented on a standard personal computer, produces values of visual perceptive attributes which characterize the perception of each hue introduced as input through its optical data. It takes into account, during simulation of the perception of each hue, of the real observation conditions. In particular, it is considered that the hue sample is observed inside a light booth with white and diffusing walls. In the mode of implementation of the invention which is described here, the perceptive attribute value which is used is that of the hue angle H which may be read off from the NCS system. It varies according to a circle between 0° and 360°, the values 0°, 90°, 180° and 270° corresponding respectively to the colors red, yellow, green and blue, and the hue varying continuously between these colors for intermediate values of H. The hue angle H is therefore particularly appropriate for distinguishing the samples within the NCS series used.

In parallel, optical data relating to each hue sample are calculated, which correspond to this sample when it is observed directly, that is to say without interposition of the color filter, while using the same illuminating light source as previously. Trichromatic components $X_0, Y_0, Z_0$ are thus calculated for each hue sample used (step 2a). They are then introduced into the CIECAM02 model to obtain a value $H_0$ of a hue angle which characterizes the visual perception of the sample (step 3a). Given that steps 1a, 2a and 3a relate to the samples of hues independently of the color filter which is currently being evaluated, they may be executed beforehand and the values which are obtained are repeated so as to successively evaluate several filters.

Figure 2A:
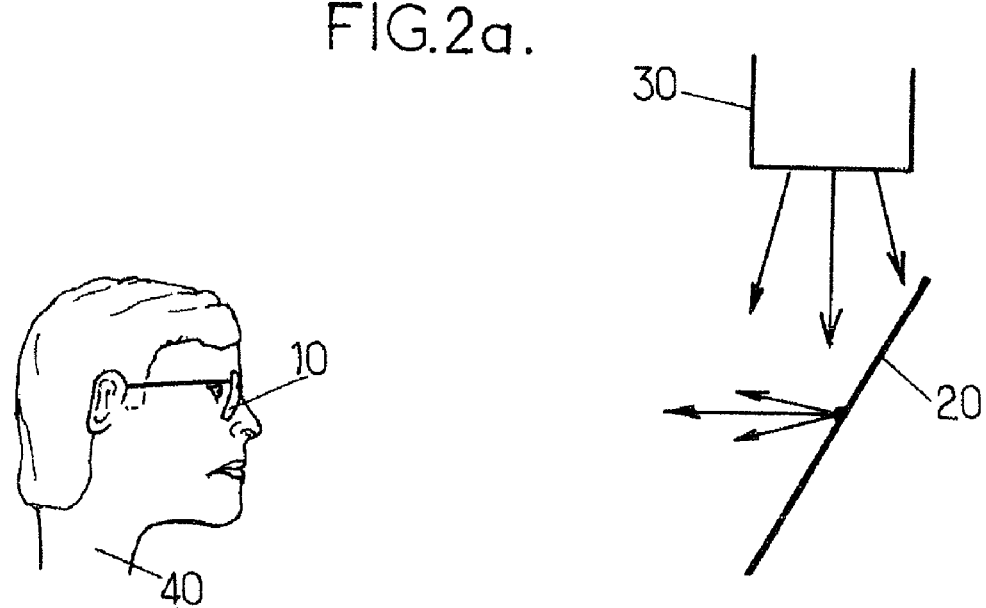
FIGS. 2a and 2b illustrate observation conditions which are considered for evaluating a color filter in accordance with the invention.
Figure 2B:

FIGS. 2a and 2b illustrate the observation conditions which correspond respectively to the values H and $H_0$ for each hue sample. The hue sample 20 is illuminated by the light source 30, which possesses an emission spectrum corresponding to the illuminant used for the calculation of the components X, Y, Z. The value H, such as it results from steps 2 and 3, corresponds to the case where the sample 20 is looked at by the observer 40 through the color filter 10, the filter 10 being disposed between the sample 20 and the eye of the observer 40. By way of illustration, FIG. 2a illustrates a case where the color filter 10 is a tinted ophthalmic lens, in particular a lens of sunglasses. However, the filter 10 may also be, in an equivalent manner, a tinted helmet visor, a protective mask glass, a filter of an optical measuring or sighting apparatus, etc. FIG. 2b illustrates the observation conditions which correspond to the value $H_0$. They are identical to those of FIG. 2a, when dispensing with the filter 10.

Returning to FIG. 1, during step 4, a difference is calculated for each hue sample, between the hue angle value H which corresponds to this sample when it is observed through the filter and the value $H_0$ which corresponds to the same sample observed without the filter. FIG. 3 is a diagram which groups together the difference values $H-H_0$ obtained for the 40 samples of hues of an NCS series used (solid curve). The samples are labelled as abscissa by a numbering of the latter in the NCS series, and the corresponding differences $H-H_0$ are labeled as ordinate. Such a diagram provides a representation of the modification of the perception of hues which is caused by the color filter. In this diagram, a curve close to the abscissa axis indicates that the filter affords a natural perception of hues, with a much reduced alteration thereof. Parts of the curve which have positive ordinate values correspond to hues which are perceived in an offset manner when rotating clockwise around the NCS circle. Conversely, parts of the curve with negative ordinate values correspond to hues which are perceived in an offset manner when rotating in the trigonometric direction around the NCS circle.

For each hue sample, the absolute value of the difference $H-H_0$, denoted $|H-H_0|$, constitutes an evaluation of the restitution of the hue of this sample by the filter. A low value of $|H-H_0|$, typically less than 0.1, indicates that the color filter hardly modifies the perception of the hue of the sample, and a high value (greater than 0.1 in particular) indicates a significant modification.

The restitution by the filter of the hue of each sample has also been evaluated by a set of human observers. Fifteen real observations were carried out for each sample, without and with the color filter interposed between the observer and the hue sample. The background luminance used for these observations is 1500 cd/m² (candela per square meter). In each case and for each hue sample, an average of the results of fifteen evaluations performed by the observers was calculated and then plotted in FIG. 3 (dashed curve). The similarity of the respective variations of the two curves of FIG. 3 constitutes a validation of the CIECAM02 hue appearance model in accounting for the perception by the human eye of variations of hues.

The global restitution of hues by the filter may be evaluated by calculating an average of the absolute values of the perceptive attribute deviations which are obtained respectively for the hue samples (step 5). Thus, the result of the evaluation of the filter, denoted R, is equal to $\Sigma_{\{samples\}}|H-H_0|/N$, where N is the number of hue samples which were used to evaluate the filter. For example, N may be equal to 40 when a complete series of NCS hue samples has been used. Other equivalent formulae may be adopted alternatively for the evaluation result R.

When several filters have each been evaluated in the manner described previously, so as to obtain respective evaluation results R for them, it is possible to rank these filters in ascending order of the results R. The filters which appear first in this ranking restore the hues in a more natural manner, whereas those at the end of the ranking alter the perception of hues more. FIG. 4 reproduces a diagram in which the results R are plotted for 6 filters, referenced 1 to 6, which were evaluated according to the method of the invention. Filters 2 and 5, for which R is substantially equal to 0.020 and 0.035 respectively, afford a rendition of hues that is in general more natural than filters 1, 3, 4 and 6, for which the values of R are of the order of 0.15.

Furthermore, for each of the filters 1 to 6, several results R were calculated using the same evaluation method, but by varying the series of NCS hue samples which is used for each evaluation. The inventors have then found that the results R which are thus obtained vary little. Stated otherwise, the evaluation of the global restitution of hues by a filter depends only weakly on the brightness and saturation of these hues. In particular, the ranking of the filters is modified possibly by varying the series of NCS samples used only if two filters are substantially equivalent as regards their respective capacities to restore the hues. This verification constitutes a validation for limiting to a single NCS series the hue samples which are used to evaluate a color filter in accordance with the invention.

The invention claimed is:

1. Method of quantitatively evaluating a color filter, comprising the following steps:
   /1/ measuring a transmission spectrum of the filter over a visible light interval using a spectrophotometer;
   /2/ obtaining, on the basis of the transmission spectrum of the filter and of a reflection spectrum of a reference hue sample, optical data relating to a simulation of an observation of the hue sample through the filter;
   /3/ introducing, into a numerical color appearance model, the optical data relating to the simulation of the observation of the hue sample through the filter, so as to obtain, for said sample, a value of at least one visual perceptive attribute; and
   /4/ calculating a deviation between the perceptive attribute value obtained for the simulation of the observation of the hue sample through the filter and a value of said perceptive attribute for an observation of the same sample without the filter,
   said deviation forming an evaluation of the restitution of the hue of the reference sample by the color filter.

2. Method according to claim 1, wherein steps /2/ to /4/ are repeated for several reference hue samples so as to obtain respective deviations of perceptive attribute for said hue samples, and wherein the method furthermore comprises the following step:
   /5/ calculating a value characterizing the global restitution of hues by the color filter on the basis of the set of perceptive attribute deviations obtained respectively for the hue samples used.

3. Method according to claim 2, wherein the value characterizing the global restitution of hues by the filter as calculated in step /5/ is equal to an average of absolute values of the perceptive attribute deviations obtained respectively for the hue samples used.

4. Method according to claim 1, wherein the optical data obtained in step /2/ are trichromatic components relating to the simulation of the observation of the hue sample through the filter.

5. Method according to claim 1, wherein the numerical hue appearance model used in step /3/ is the CIECAM02 model.

6. Method according to claim 1, wherein the visual perceptive attribute value obtained in step /3/ is a value of hue angle H which may be read off from the NCS system.

7. Method according to claim 1, wherein the reflection spectrum of the hue sample used in step /2/ is a nonspecular reflection spectrum.

8. Method according to claim 1, wherein the optical data obtained in step /2/ correspond to the "SoLux Daylight" illumination conditions.

9. Method of quantitatively evaluating a hue restitution by a tinted ophthalmic lens according to claim 1.

10. Method of ranking color filters, wherein several color filters are evaluated successively using an evaluating method according to claim 1, and wherein said filters are ranked as a function of the evaluation results obtained respectively for said filters.

11. Method of ranking tinted ophthalmic lenses according to claim 10.

* * * * *

UNITED STATES PATENT AND TRADEMARK OFFICE
CERTIFICATE OF CORRECTION

PATENT NO. : 7,659,982 B2  Page 1 of 1
APPLICATION NO. : 11/839099
DATED : February 9, 2010
INVENTOR(S) : Gilles Baillet et al.

It is certified that error appears in the above-identified patent and that said Letters Patent is hereby corrected as shown below:

On the title page item (73) should read:

Essilor International (compagnie Generale D'optique), Charenton le Pont (FR)
Centre National de la Recherche Scientifique - CNRS, Paris (FR)

Signed and Sealed this
Nineteenth Day of July, 2011

David J. Kappos
*Director of the United States Patent and Trademark Office*